United States Patent [19]

Liprie

[11] Patent Number: 5,503,614
[45] Date of Patent: Apr. 2, 1996

[54] FLEXIBLE SOURCE WIRE FOR RADIATION TREATMENT OF DISEASES

[76] Inventor: Samuel F. Liprie, 424 W. McNeese St., Lake Charles, La. 70605

[21] Appl. No.: 257,045

[22] Filed: Jun. 8, 1994

[51] Int. Cl.⁶ .............................. A61M 36/00; A61N 5/00
[52] U.S. Cl. ...................................... 600/7; 600/8
[58] Field of Search ................................. 600/1–8

[56] References Cited

U.S. PATENT DOCUMENTS

| | | | |
|---|---|---|---|
| 3,351,049 | 11/1967 | Lawrence | 600/8 |
| 4,763,642 | 8/1988 | Horowitz | 600/7 |
| 4,819,618 | 4/1989 | Liprie . | |
| 4,861,520 | 8/1989 | van't Hooft et al. . | |
| 4,891,165 | 1/1990 | Suthanthiran | 600/8 |
| 5,084,002 | 1/1992 | Liprie . | |
| 5,141,487 | 8/1992 | Liprie . | |
| 5,282,781 | 2/1994 | Liprie . | |
| 5,342,283 | 8/1994 | Good | 600/8 |

Primary Examiner—Angela D. Sykes
Assistant Examiner—Samuel Gilbert
Attorney, Agent, or Firm—Hoffman, Wasson & Gitler

[57] ABSTRACT

A flexible source wire is provided containing a radioactive source that is capable of maneuvering through a tortuous narrow passage to a treatment site within the body. This source wire includes a thin flexible housing tube, housing therein a flexible backbone wire, both the tube and the wire being constructed from a material exhibiting little or no memory retention when bent. A radioactive source is provided in the proximal end of the thin flexible housing tube. This radioactive source is contained in a capsule abutting the proximal end of the backbone wire all within a thin wall encapsulating material. Both ends of the source wire are welded shut to form a tight seal and rounded to allow ease of movement as it travels through the bends and turns in the body. The housing tube is coated before the loading of the radioactive material with a non-oxidizing agent such as gold.

38 Claims, 2 Drawing Sheets

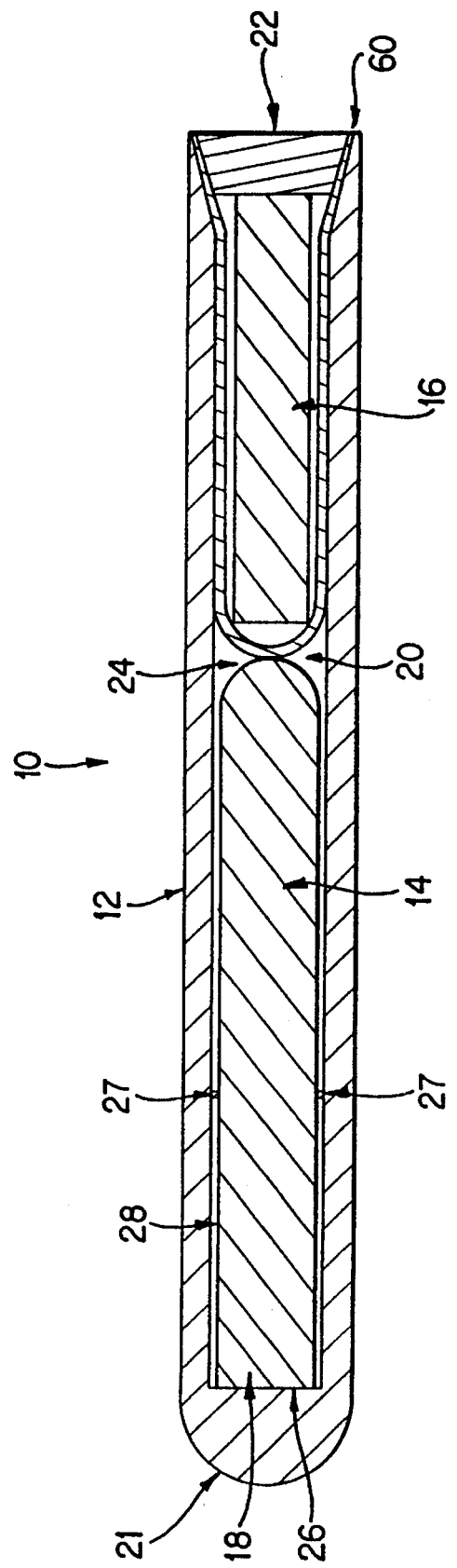

FLEXIBLE SOURCE WIRE FOR RADIATION TREATMENT OF DISEASES

BACKGROUND OF THE INVENTION

1. Field of the Invention

The present invention relates to the use of radioactive sources to treat diseases of the body. More particularly, the present invention relates to the use of a flexible member housing a radioactive source for the temporary delivery of radiation to treat diseases of the body.

2. Description of the Prior Art

Radiation is used to treat cancer and other diseases of the body. Radiation has long been proven to destroy fast multiplying cells (e.g., cancer) in hopes of destroying or preventing the spread of the disease. Brachytherapy, which is the treatment of cancer at close distances, is one example of the use of radiation for treating diseases of the body. During brachytherapy, a radioactive source or sources are positioned in the area needing treatment. Depending on the shape, size and delivery means of the radioactive sources, the sources are either kept permanently in the body or removed after a specific amount of time. Since permanent implants are tiny seeds approximately 3 mm long and 0.5 mm wide, the use of these seeds do not relate to the present invention. Consequently, the focus of this application will be on the field of temporary implants.

The term temporary implants describes the procedure of maneuvering a radioactive source or sources to the treatment site utilizing a transport catheter or tube which has been previously placed in the vicinity of this treatment site. Alternatively, the transport catheter and temporary implant can simultaneously be maneuvered to the treatment site. In either situation, after a specified period of time, these sources and the transport catheter or tube are removed from the body. Since the radioactive source or sources may encounter a tortuous path in various arteries, veins, ducts, or the like inside the body to reach the treatment site, the radioactive source is usually attached by some device to a flexible drive member. This source and the drive member may be used many times, and, therefor must be able to withstand the many bends it encounters when it is maneuvered to the treatment site or removed therefrom, without breaking.

There are several devices on the market in which radioactive sources are attached to flexible drive members. Each of these devices is constructed in a different fashion and each has its limitations. Examples of these prior art devices are described in U.S. Pat. No. 4,819,618 and 5,141,486, both issued to Liprie as well as U.S. Pat. No. 4,861,520 issued to van't Hooft. The two Liprie patents describe a radioactive element which is attached to a drive member by means of a junction welded to the drive cable. The patent to van't Hooft describes an apparatus which attaches radioactive sources to a drive cable by means of a stiff capsule welded into the end of the cable. Since the most resistive portion to flection of any flexible material, such as a cable, tube, or wire is the segment closest to the end, to join a capsule which is stiffer than this material and welded onto its end would only add to the resistance to bending and would adversely effect maneuvering the material through the body.

U.S. Pat. No. 5,084,002 issued to Liprie describes an ultra-thin high dose iridium source included within an oversized hole drilled inside the end of a solid platinum wire. The whole assembly is then drawn down to the desired diameter of the wire. While this patent does not describe the situation in which a radioactive source is joined to the end of a solid cable, the platinum delivery wire would still present problems with respect to maneuvering the wire through the numeral twists and turns in the body.

Finally, U.S. Pat. No. 5,282,781 issued to Liprie employs a tube, a backbone wire, a pure iridium core and a plug and draws down the entire assembly to form a tight seal between the housing material and the backbone wire and the plug. Without this drawing down of the housing onto the backbone wire, radioactive flakes from the core would migrate throughout the inside of the assembly wire, resulting in unwanted contamination. This "drawing down" step would increase the costs and difficulty of manufacturing the source wire.

SUMMARY OF THE INVENTION

These and other deficiencies of the prior art are addressed by the present invention which is directed to a flexible source wire for the radiation treatment of disease in which the source wire contains a radioactive source and is maneuvered to the site of treatment through various conduits in the body. The flexible source wire includes a flexible housing in the form of an elongated hollow tube constructed from a material such as Nitinol® or a titanium/nickel alloy which exhibits little or no memory retention when it is bent. An internal flexible backbone wire also constructed from the same material as the flexible tube which exhibits little or no memory retention. The backbone wire is provided within the flexible tube.

A thin-walled capsule or encapsulated radioactive core as well as a plug is also provided within the flexible tube. The backbone wire is welded to the distal end of the tube and runs throughout the length of the flexible tube to a distance just short of the proximal end of the tube. The radioactive capsule or encapsulated radioactive core which is provided in the proximal portion of the flexible tube, abuts the end of the backbone wire. The encapsulating material must have a very thin wall to allow flexibility. This thin wall should be constructed from material that will block very little of the neutron flux as the core is being irradiated, as well as not becoming radioactive or exhibit an insignificant amount of radioactivity after a period of approximately 20 days. A good example of this material is titanium, platinum, gold or high purity aluminum such as aluminum 1100.

A plug is provided at the proximal end of the tube to seal the radioactive capsule or the encapsulated radioactive core within the tube. Mounting the radioactive source into the segment of a tube which is naturally stiff would not add any appreciable resistance to bending, in contradistinction to the Liprie '618 and Liprie '487 patents, as well as the patent to van't Hooft. Since material such as Nitinol® as well as a titanium/nickel alloy which exhibits little or no memory retention when bent have dissimilar welding properties than other metals, they do not form a strong bond against the stress of repeated bending. This feature would reduce the possibility that the device is prone to breakage.

Furthermore, due to the characteristics of "little or no memory" material such as Nitinol®, a titanium/nickel alloy, etc., the "drawing down" of the material illustrated in Liprie '781 is not possible. Furthermore, providing a source wire as illustrated in Liprie '002 in which an iridium source is inserted into a hole which is drilled into the end of a thin wire is not necessary. Drilling a hole into a thin wire is very difficult since the maximum depth the hole can be drilled is equal to approximately seven times the outside diameter of the wire. To drill a hole deeper than this distance is extremely difficult due to the drifting of the drill as its burrows the hole. This drifting can lead to a thinning of the cavity walls which greatly increases the chances of breakage. This breakage is often disastrous, resulting in unwarranted radiation exposure. A larger outside diameter wire will be needed to compensate for the drifting and still allow the walls of the cavity to be thick enough to withstand stress. Unfortunately, this larger diameter wire might be too large to fit into many constricted areas of the body. Additionally, this larger diameter wire would result in less flexibility and may not be able to be maneuvered to the treatment site. Another method of drilling the cavity inside a solid wire, would be to start with an oversize wire and an oversize hole and draw the entire structure down to size. Whenever a wire is drawn down, the assembly containing the cavity elongates and precise positioning of the radioactive core inside the assembly can become very difficult. Utilizing a tube as the flexible source as is utilized in the present invention would eliminate the need for this type of drilling.

BRIEF DESCRIPTION OF THE DRAWINGS

These and other attributes of the present invention will be described with respect to the following drawings in which:

FIG. 3 is a partial cross-section of the present invention provided with a proximal end having a funnel shape.

DETAILED DESCRIPTION OF THE INVENTION

Figure 1:
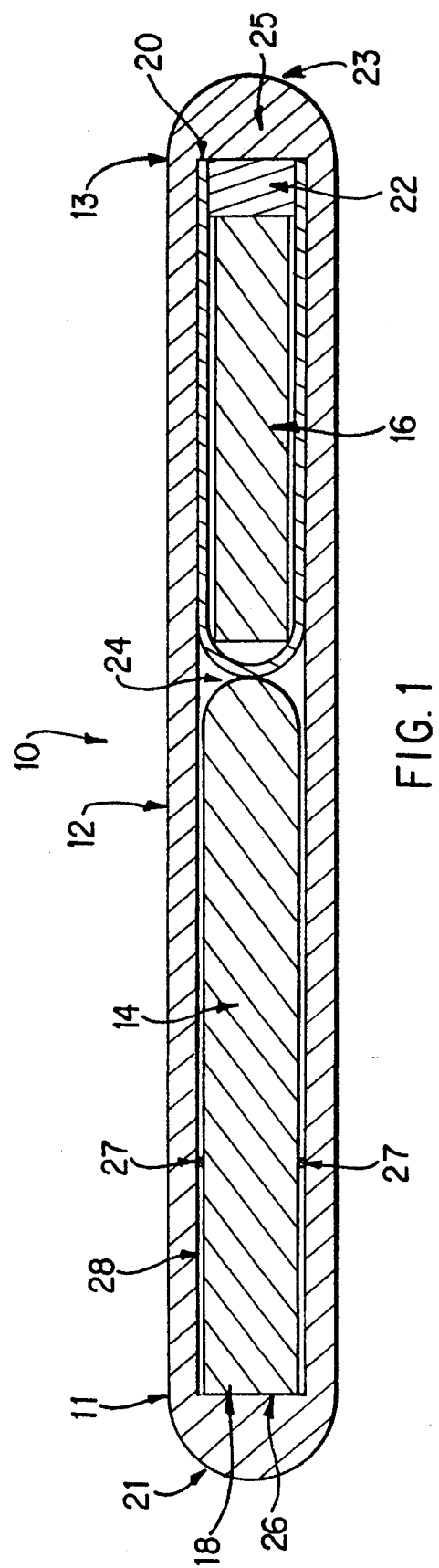
FIG. 1 is a partial cross-section of the invention showing a radioactive core inside a thin wall capsule provided within the flexible source tube.

FIG. 1 illustrates a first embodiment of the present invention 10 utilizing a radioactive core 16 provided within a thin-walled capsule. This embodiment employs an elongated hollow housing tube 12 constructed from a material such as Nitinol®, a titanium/nickel alloy or similar materials which exhibit little or no memory retention when the tube is bent. Since this housing tube is used to maneuver the radioactive core to a remote treatment site, the length of the tube is generally greater than 100 cm and, could extend for a much greater distance. Additionally, since the housing tube must be maneuvered within various twists and turns in the body through various conduits therein, the diameter of this tube could range from 0.018"to 0.023".

A flexible backbone wire 14 is provided between the distal end 11 of housing tube 12 and extends to several millimeters from the end of the proximal portion 13 of the housing tube. For ease of initially inserting the backbone wire 14 into the tube 12 and to allow greater pivoting of the assembly while reducing stress to the housing material, the end 24 of this wire is rounded. Similar to the housing tube 12, this backbone wire 14 can also be constructed from material such as Nitinol®, a titanium/nickel alloy or other materials which exhibit little or no memory retention when bent.

A capsule 20 is inserted into the proximal end of the housing tube 12 until it abuts the rounded end 24 of the backbone wire 14. The capsule should be manufactured from a very thin-walled metallic material. The radioactive core 16 is then inserted within the capsule and a plug 22 abutting the proximal end of the core 16 is provided within the capsule 20 and is used to seal the radioactive core 16 in place.

The plug 22 is sealed in place using a weld 25 or other methods of forming a tight seal. The distal end of the backbone wire 18 is welded in place at 26. Both ends 21, 23 of the housing tube 12 are rounded to allow ease of movement as it travels through bends and turns in the body. The exterior of the housing tube 12 is coated prior to the loading of the radioactive core 16 with a non-oxidizing agent, such as gold. The backbone wire 14 can be welded, fused or glued to different areas of the inner tube, such as 27 to serve as an internal safety and protection device. If the outer tube 12 breaks, the radioactive source 16 would still be able to be retracted. For ease of inserting the backbone wire 14 into the interior of the tube 12, a small gap 28 between the inner surface of the tube and the outer surface of the wire is provided. The outside diameter of the capsule 20 should fit snugly against the inside diameter of the tube 12. However, it is noted that a small gap can also be included between the capsule 20 and the interior wall of the tube 12.

Figure 2:
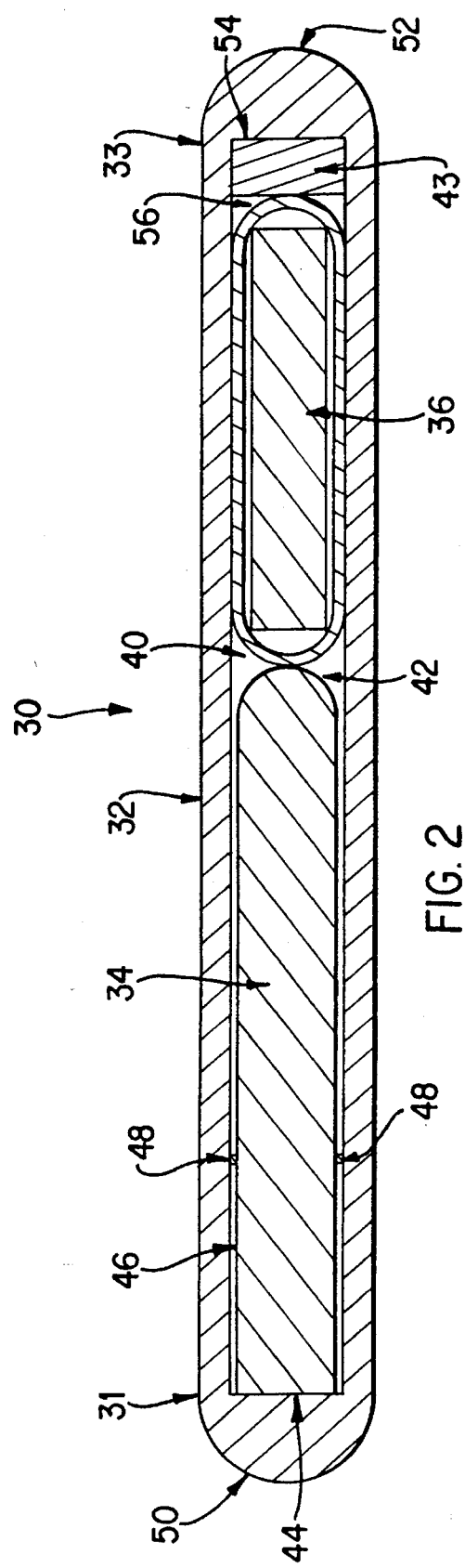
FIG. 2 is a partial cross-section of the present invention showing the use of the encapsulated core within the flexible source tube.

FIG. 2 illustrates a second embodiment 30 of the present invention utilizing an elongated cylindrical housing tube 32 similar in dimension to the tube described with respect to FIG. 1. This tube is constructed from material such as Nitinol®, titanium/nickel alloy or a similar material which exhibits little or no memory retention when bent. A backbone wire 34 constructed from the same material as the housing tube 32 is introduced to the interior of the housing tube 32 and extends from the distal end 31 thereof to an area positioned several millimeters from the proximal end 33 of the tube. The backbone wire 34 is provided with rounded end 42 to aid in movement within the tube 32. A source of radioactivity 36 is provided within a thin wall encapsulating material 40 so that it abuts the rounded end 42 of the backbone wire 34. This thin material 40 should allow the passage of neutrons to irradiate the inner core but the same time this material should obtain no significant radioactivity. The radioactive treatment to be delivered must come from the radiation exposure of the inner core 36 and not from the radiation exposure of the encapsulation material 40. The encapsulation material should be flexible. A good example of this material would be platinum, gold, titanium, or high purity aluminum such as aluminum 1100.

The backbone wire 34 is introduced into the distal end of the housing tube 32 and is welded in place by weld 44. Additionally, the backbone wire 34 can be affixed to various inner surfaces of the housing tube 32 such as at spot 48 by welding, fusing, pasting or other methods. A small gap 46 is provided between the outer surface of the backbone wire 34 and the inner surface of the housing tube 32. This gap aids in allowing the backbone wire 34 to be moved to its proper position within the housing tube 32. The encapsulated core is introduced into the interior of the housing tube 32 at its proximal end so that it abuts the rounded edge 42 of the backbone wire 34. A plug 43 is then loaded into the proximal end of the housing tube 32 so that it abuts the rounded proximal end 56 of the encapsulated core. The plug is then welded in place by weld 54. Both the proximal and distal ends of the housing tube 32 are rounded at 50, 52 to aid in the maneuverability of the housing tube 32 within the body. Furthermore, similar to the embodiment illustrated in FIG. 1, the outer surface of the housing tube 32 is coated with a non-oxidizing agent such as gold.

FIG. 3 illustrates a flexible source wire similar in many respects to the embodiments shown in FIGS. 1 and 2. In this embodiment, similar elements in FIG. 1 will have the same reference numerals as their respective elements in FIG. 3.

Furthermore, although the embodiment shown in FIG. 3 illustrates a flexible source wire utilizing a radioactive core within a capsule, these teachings can also be applied to the situation in which the radioactive core is encapsulated.

After the backbone wire 14 is inserted through the distal end of the housing tube 12 and properly affixed in place, the capsule 20 is introduced into the proximal end of the housing tube 12 by utilizing a styler. The inner portion of the wall of the housing tube 12 exhibits a slightly tapered funnel shape 60 or is countersunk at the proximal end of the tube to aid in the introduction of the capsule. Similarly, the encapsulated radioactive core shown in FIG. 2 can be introduced into a tube having a slight funnel shape at its proximal end. Once the capsule is in place, the radioactive core 16 is introduced therein manually utilizing a tweezers or automatically employing a similar device in a robot handling system. Once the capsule 20 and the radioactive core 16 or the encapsulated core 36 is introduced into the proximal end of its respective tube until it abuts the proximal end of its respective backbone wire, a plug is loaded in place and then sealed.

Having described several embodiments of the new and improved flexible source wire for radiation treatment in accordance with the present invention, it is believed that other modifications, variations and changes will be suggested to those skilled in the art in view of the description set forth above. It is therefor to be understood that all such variations, modifications and changes are believed to fall within the scope of the invention as defined in the appended claims.

What is claimed is:

1. A flexible source wire for radiation treatment of diseases within a body comprising:

a flexible, hollow, elongated housing tube having an outer surface, an interior wall surface, a distal end, and a proximal end, said proximal end having an inner surface, said housing tube constructed from a material exhibiting little or no memory retention allowing said elongated housing tube to return to its original shape after being bent;

a flexible backbone wire having a proximal end, said flexible backbone wire provided within said housing tube and constructed from material exhibiting little or no memory retention allowing said backbone wire to return to its original shape after it is bent;

a sealing device provided within said housing tube; and a radiation device provided within said housing tube, said radiation device included within said sealing device.

2. The flexible source wire in accordance with claim 1 further including a plug which is sealed to said proximal end of said housing tube.

3. The flexible source wire in accordance with claim 1 wherein said sealing device is a capsule having a distal end which is inserted into said housing tube prior to said radiation device being inserted into said housing tube.

4. The flexible source wire in accordance with claim 3 wherein said housing tube is constructed from an alloy comprising approximately 50% titanium and approximately 50% nickel.

5. The flexible source wire in accordance with claim 3 further including a means for reducing stress and for allowing greater pivoting of the flexible source wire at said proximal end of said flexible backbone wire and said distal end of said capsule.

6. The flexible source wire in accordance with claim 5 wherein said means for reducing stress and for allowing greater pivoting includes a rounded end of said backbone wire and a rounded end of said capsule adjacent to said rounded end of said backbone wire.

7. The flexible source wire in accordance with claim 1 further including a means forming a backup safety and protection device to ensure that said backbone wire remains in place within said housing tube.

8. The flexible source wire in accordance with claim 7 wherein said means forming a backup safety and protection device includes affixing said backbone wire to said interior wall surface of said flexible housing tube at one or more locations.

9. The flexible source wire in accordance with claim 1 wherein said sealing device is thin-walled material which completely encapsulates said radiation device prior to inserting said radiation device into said housing tube, said sealing device having a proximal end and a distal end.

10. The flexible source wire in accordance with claim 9 wherein said housing tube is constructed from an alloy comprising approximately 50% titanium and approximately 50% nickel.

11. The flexible source wire in accordance with claim 9 wherein said sealing device is constructed from a material selected from the group consisting of titanium, platinum, and high purity aluminum.

12. The flexible source wire in accordance with claim 4 further including a means for reducing stress and allowing greater pivoting of the flexible source wire at said proximal end of said backbone wire and said distal end of said radiation device.

13. The flexible source wire in accordance with claim 12 wherein said means for reducing stress and allowing greater pivoting includes a rounded end of said backbone wire and a rounded end of said encapsulated radiation device in proximity to said rounded end of said backbone wire.

14. The flexible source wire in accordance with claim 1 wherein said housing tube is constructed from an alloy comprising approximately 50% titanium and approximately 50% nickel.

15. The flexible source wire in accordance with claim 1 wherein a portion of said inner surface of said proximal end of said housing tube exhibits a tapered funnel shape for ease of loading said radiation device within said flexible housing tube.

16. The flexible source wire in accordance with claim 1 wherein said outer surface of said housing tube is coated with a non-oxidizing agent.

17. The flexible source wire in accordance with claim 16 wherein said non-oxidizing agent is gold.

18. The flexible source wire in accordance with claim 1 wherein said flexible backbone wire is affixed to the interior wall of said flexible housing tube at one or more locations to prevent migration of said radiation device throughout the flexible source wire.

19. A flexible source wire for the radiation treatment of diseases within a body comprising:

a flexible, hollow, elongated housing tube having an outer surface, an interior wall surface, a distal end, and a proximal end, said proximal end having an inner surface;

a backbone wire having a proximal end, provided within said housing tube;

a capsule inserted into said proximal end of said flexible elongated housing tube, said capsule provided with a distal end;

a radioactive device inserted into said capsule; and a plug which seals said proximal end of said housing tube.

20. The flexible source wire in accordance with claim 19 wherein said housing tube is constructed from an alloy comprising approximately 50% titanium and approximately 50% nickel.

21. The flexible source wire in accordance with claim 19 wherein a portion of the inner surface of said proximal end of said housing tube exhibits a tapered funnel shape for ease of loading said radiation device within said flexible housing tube.

22. The flexible source wire in accordance with claim 19 wherein the outer surface of said housing tube is coated with a non-oxidizing agent.

23. The flexible source wire in accordance with claim 22 wherein said non-oxidizing agent is gold.

24. The flexible source wire in accordance with claim 19 further including a means for reducing stress and allowing greater pivoting of the flexible source wire at said proximal end of said flexible backbone wire and said distal end of said capsule.

25. The flexible source wire in accordance with claim 19 wherein said means for reducing stress and allowing greater pivoting includes a rounded end of said backbone wire and a rounded end of said capsule adjacent to said rounded end of said backbone wire.

26. The flexible source wire in accordance with claim 19 further including a means forming a backup safety and protection device to ensure that said backbone wire remain in place within said housing tube.

27. The flexible source wire in accordance with claim 19 wherein said means forming a backup safety and protection means includes affixing said backbone wire to said interior wall surface of said flexible housing tube at one or more locations.

28. The flexible source wire in accordance with claim 19 wherein said flexible backbone wire is affixed to the interior wall of said flexible housing tube at one or more locations to prevent migration of said radiation device throughout the flexible source wire.

29. A flexible source wire for radiation treatment of diseases within a body comprising:

a flexible, hollow, elongated housing tube having an outer surface, an interior wall surface, a distal end, and a proximal end, said proximal end having an inner surface;

a backbone wire inserted into said elongated flexible housing tube;

a radiation device comprising a source of radiation and encapsulating material wherein said source of radiation is encapsulated in said encapsulating material to provide a sealed source of radiation, said sealed source of radiation provided with a distal end, said radiation device provided within said housing tube; and a plug which seals said proximal end of said housing tube.

30. The flexible source wire in accordance with claim 29 wherein said housing tube is constructed from an alloy comprising approximately 50% titanium and approximately 50% nickel.

31. The flexible source wire in accordance with claim 29 wherein a portion of the inner surface of said proximal end of said housing tube exhibits a tapered funnel shape for ease of loading said radiation device within said flexible housing tube.

32. The flexible source wire in accordance with claim 29 wherein the outer surface of said housing tube is coated with a non-oxidizing agent.

33. The flexible source wire in accordance with claim 32 wherein said non-oxidizing agent is gold.

34. The flexible source wire in accordance with claim 29 further including a means for reducing stress and allowing greater pivoting of the flexible source wire said proximal end of said flexible backbone wire and said distal end of said sealed source of radiation.

35. The flexible source wire in accordance with claim 29 wherein said means for reducing stress and allowing greater pivoting includes a rounded end of said backbone wire and a rounded end of said sealed source adjacent to said rounded end of said backbone wire.

36. The flexible source wire in accordance with claim 29 further including a means forming a backup safety and protection device to ensure that said backbone wire remains in place within said housing tube.

37. The flexible source wire in accordance with claim 29 wherein said means forming a backup safety and protection device includes affixing said backbone wire to said interior wall surface of said flexible housing tube at one or more locations.

38. The flexible source wire in accordance with claim 29 wherein said flexible backbone wire is affixed to the interior wall of said flexible housing tube at one or more locations to prevent migration of said radiation device throughout the flexible source wire.

* * * * *

UNITED STATES PATENT AND TRADEMARK OFFICE
CERTIFICATE OF CORRECTION

PATENT NO.    : 5,503,614
DATED         : April 2, 1996
INVENTOR(S)   : Samuel F. Liprie It is certified that error appears in the above-identified patent and that said Letters Patent is hereby corrected as shown below:

Column 4,
Line 26, after "bent" insert -- Nitinol® is a special alloy consisting of approximately 50% titanium and 50% nickel. This material undergoes a process that allows it to have memory resistant properties. --

Column 5,
Line 8, delete "styler" and insert therefor -- stylet --

Column 6,
Line 13, after "is" insert -- a --

Column 7,
Line 19, delete "capsule" and insert therefor -- sealed source of radiation --

Column 8,
Line 23, after "wire" insert -- at --
Line 25, delete "sealed source of radiation" and insert therefor -- capsule --

Signed and Sealed this

Twenty-first Day of August, 2001

Attest:

NICHOLAS P. GODICI
Attesting Officer   Acting Director of the United States Patent and Trademark Office